(12) United States Patent
Wettendorff (10) Patent No.: US 7,371,390 B2
(45) Date of Patent: May 13, 2008

(54) VACCINE AGAINST HBV AND HPV

(75) Inventor: Martine Anne Cecile Wettendorff, Rixensart (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 356 days.

(21) Appl. No.: 10/983,451

(22) Filed: Nov. 8, 2004

(65) Prior Publication Data

US 2005/0123562 A1   Jun. 9, 2005

Related U.S. Application Data

(63) Continuation of application No. 10/070,468, filed as application No. PCT/EP00/08728 on Sep. 6, 2000, now abandoned.

(30) Foreign Application Priority Data

Sep. 7, 1999   (GB) ................... 9921147.6

(51) Int. Cl.
*A61K 39/12* (2006.01)
(52) U.S. Cl. .................. 424/204.1; 424/227.1
(58) Field of Classification Search ............ 424/204.1, 424/227.1, 278.1
See application file for complete search history.

(56) References Cited

U.S. PATENT DOCUMENTS 5,776,468 A * 7/1998 Hauser et al. ........... 424/226.1

FOREIGN PATENT DOCUMENTS

| WO | WO 92/11291 | 7/1992 |
|----|-------------|--------|
| WO | WO 93/19780 | 10/1993 |
| WO | WO 94/21292 | 9/1994 |
| WO | WO 95/17209 | 6/1995 |
| WO | WO 95/17210 | 6/1995 |
| WO | WO 99/45957 | 9/1999 |
| WO | WO 01/17551 | 3/2001 |

OTHER PUBLICATIONS

Michel et al, Virology, 2002, vol. 294, pp. 47-59.*
Tindle, et al., "Chimeric Hepatitis B Core Antigen Particles Containing B- and Th-Epitopes of Human Papillomavirus Type 16 E7 Protein Induce Specific Antibody and T-Helper Responses in Immunised Mice". *Virology*, 200: 547-557 (1994).

* cited by examiner

*Primary Examiner*—Ali R. Salimi
(74) *Attorney, Agent, or Firm*—William R. Majarian; Stephen Venetainer; Charles Kinzig (57) ABSTRACT

Novel combined vaccine compositions are provided, comprising a hepatitis B viral antigen and optionally in addition one or more of the following: an EBV antigen, a hepatitis A antigen or inactivated attenuated virus, a herpes simplex viral antigen, a VZV antigen, a *Toxoplasma gondii* antigen. The vaccine compositions are formulated with an adjuvant which is a preferential stimulator of TH1 cell response such as 3D-MPL and QS21.

7 Claims, 10 Drawing Sheets

Figure 1:
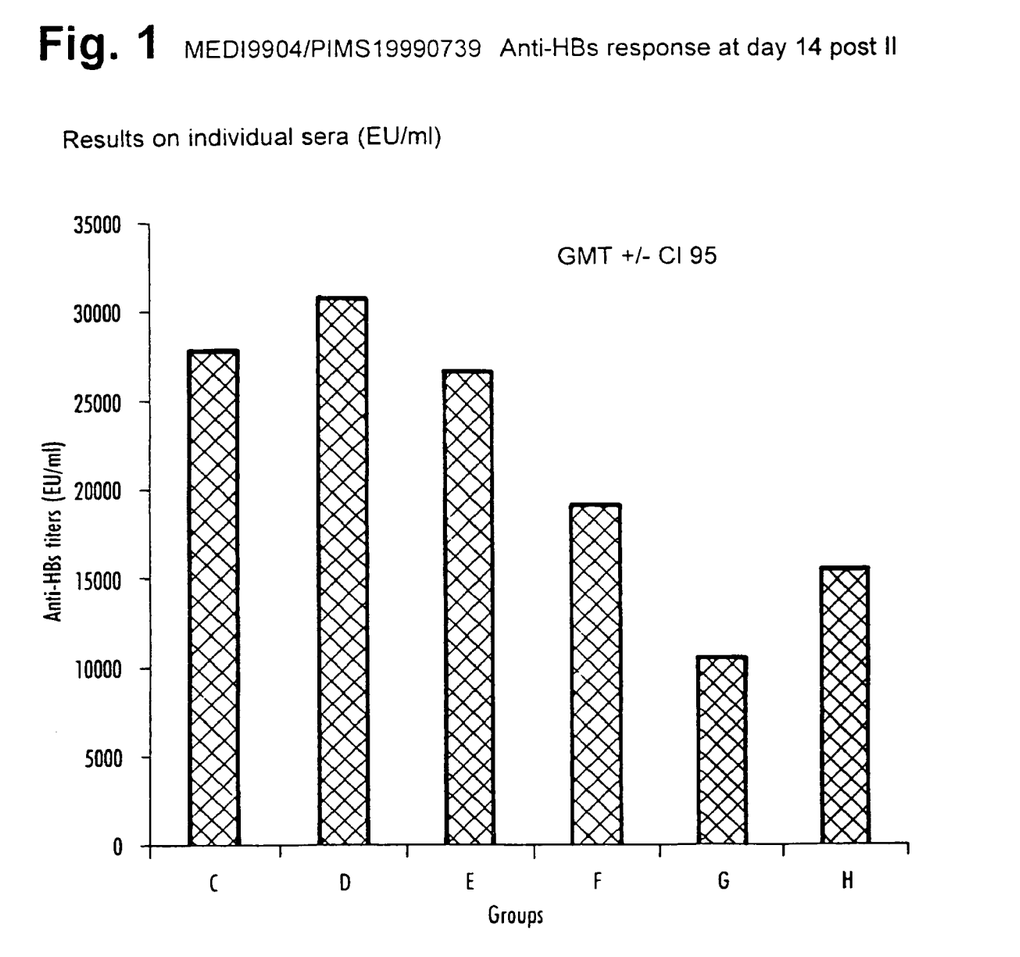

Fig. 1 MEDI9904/PIMS19990739 Anti-HBs response at day 14 post II

Figure 2:
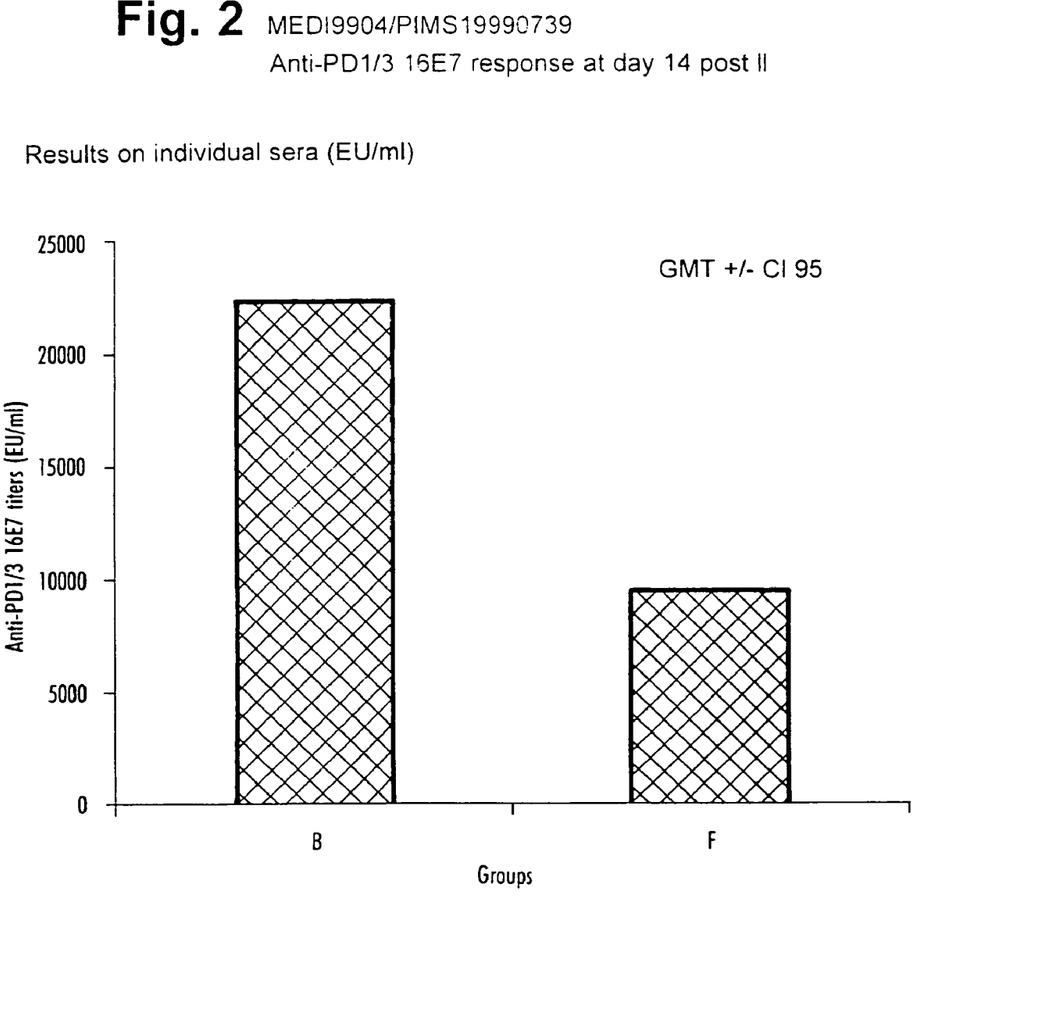

Fig. 2 MEDI9904/PIMS19990739
Anti-PD1/3 16E7 response at day 14 post II

Figure 3:
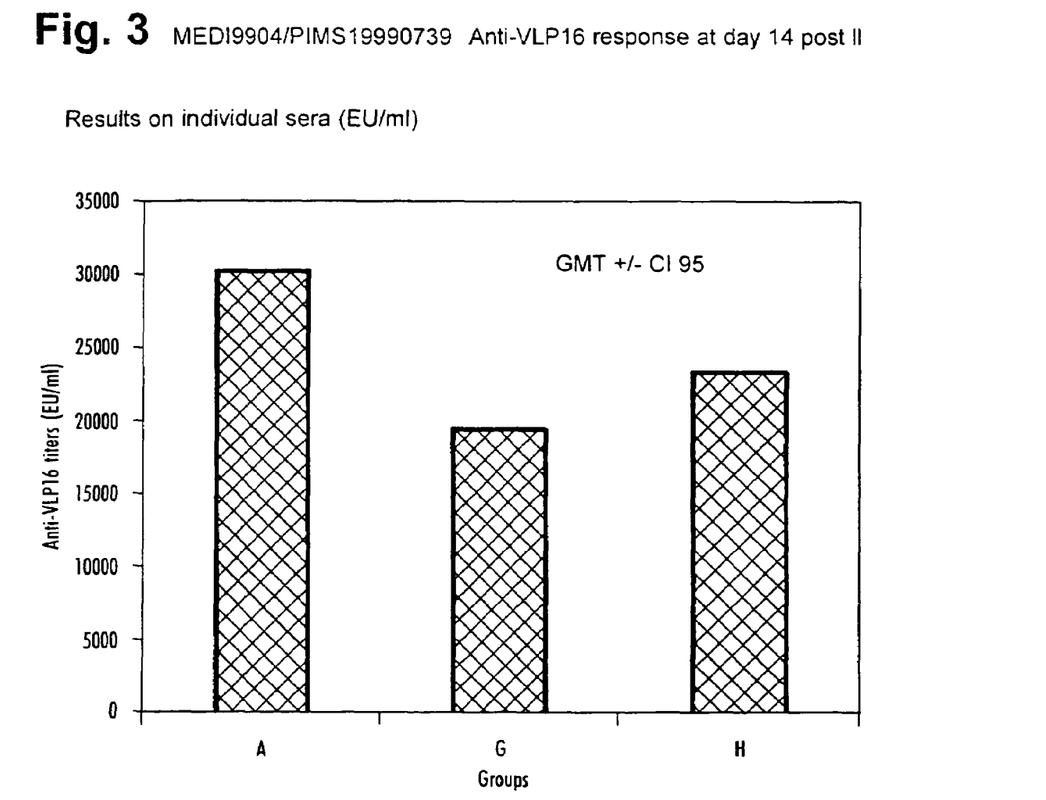

Fig. 3  MEDI9904/PIMS19990739 Anti-VLP16 response at day 14 post II

Results on individual sera (EU/ml)

Figure 4:
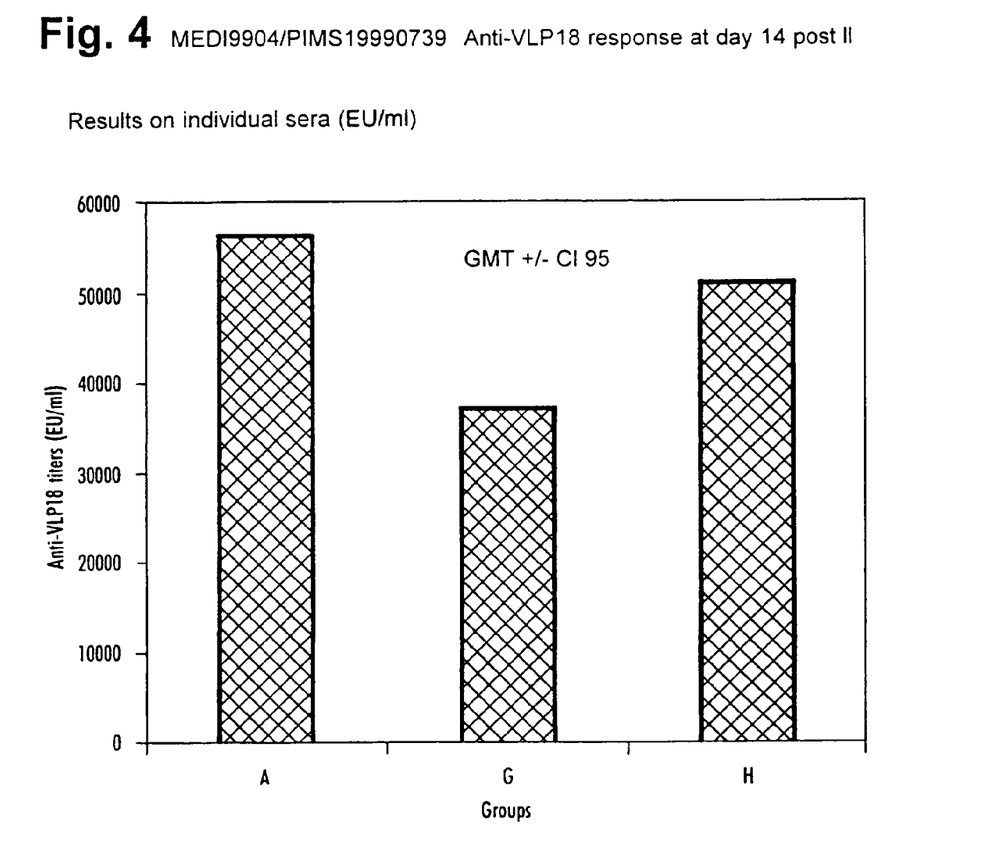

Fig. 4 MEDI9904/PIMS19990739 Anti-VLP18 response at day 14 post II

Figure 5:
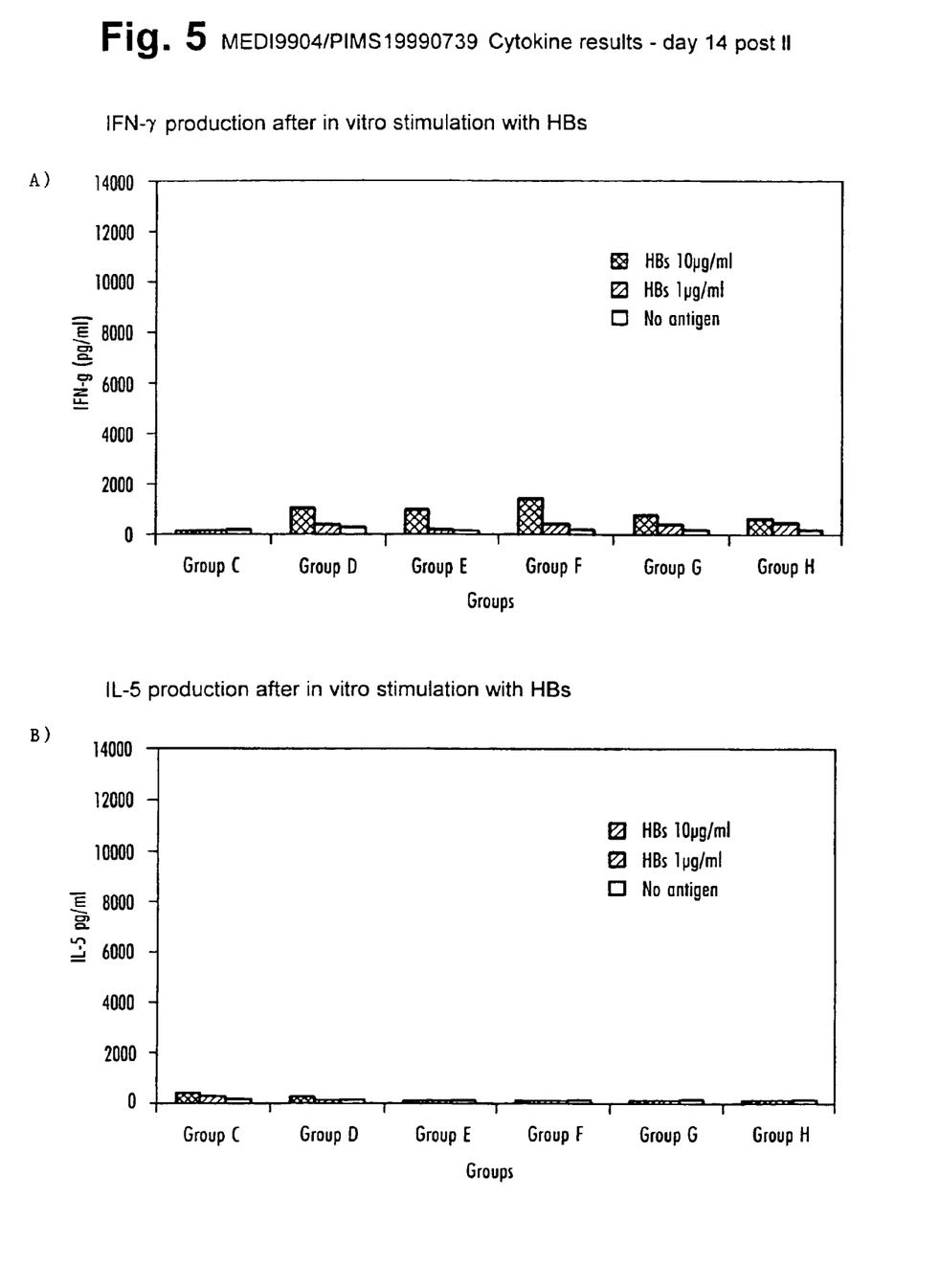

Fig. 5 MEDI9904/PIMS19990739 Cytokine results - day 14 post II

IFN-γ production after in vitro stimulation with HBs

A)

IL-5 production after in vitro stimulation with HBs

B)

Figure 6:
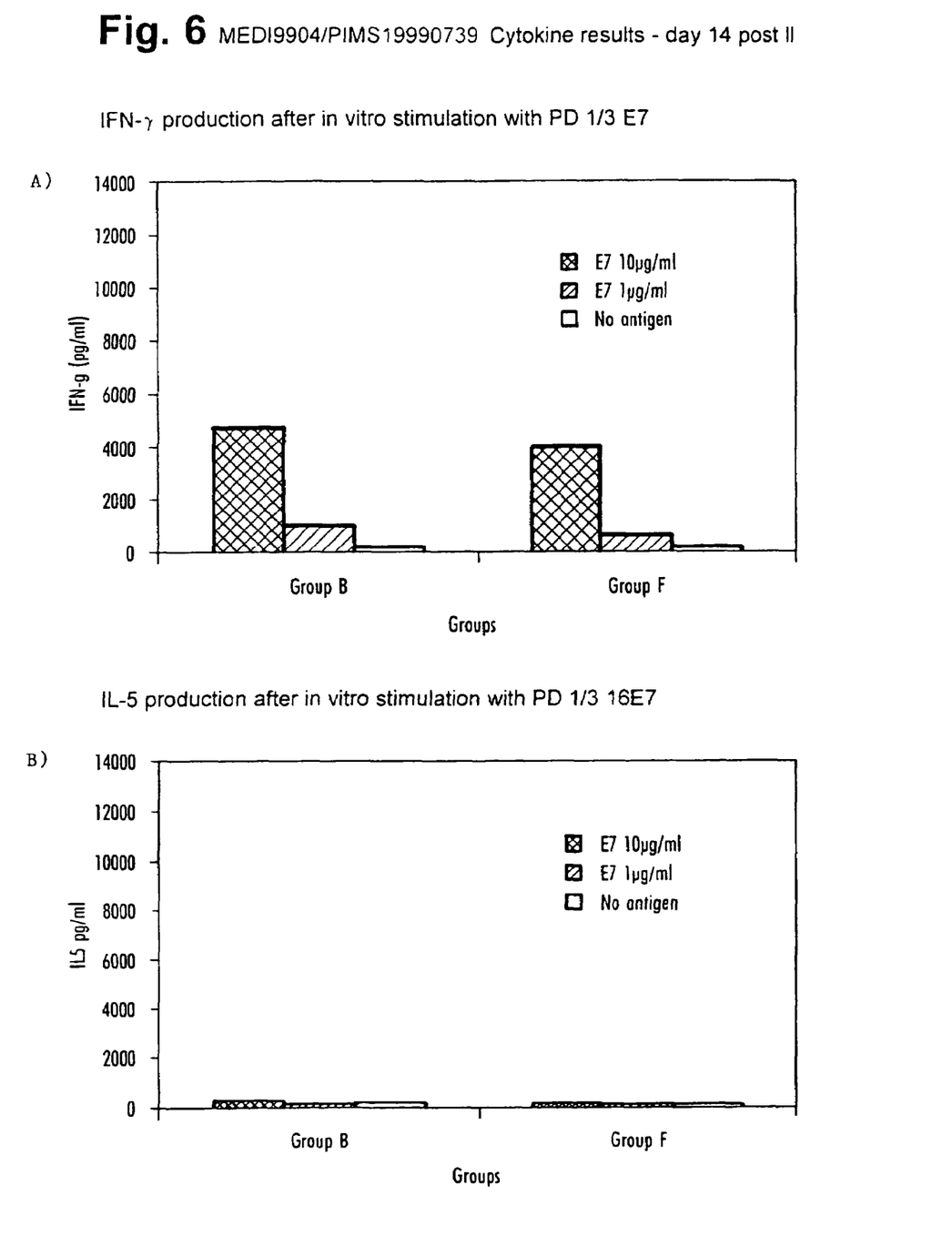

Fig. 6 MEDI9904/PIMS19990739 Cytokine results - day 14 post II

IFN-γ production after in vitro stimulation with PD 1/3 E7

A)

IL-5 production after in vitro stimulation with PD 1/3 16E7

B)

Figure 7:
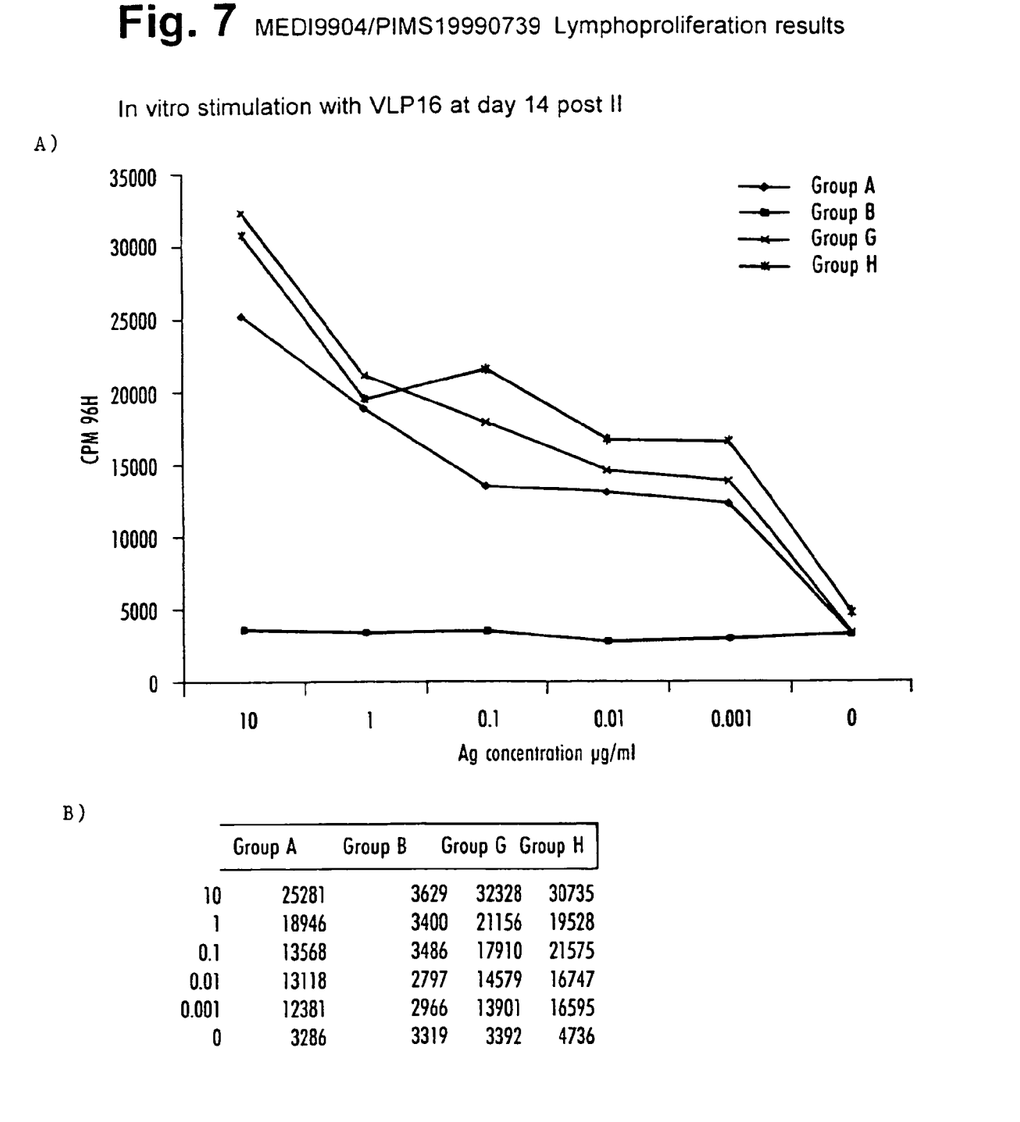

Fig. 7 MEDI9904/PIMS19990739 Lymphoproliferation results

In vitro stimulation with VLP16 at day 14 post II

Figure 8:
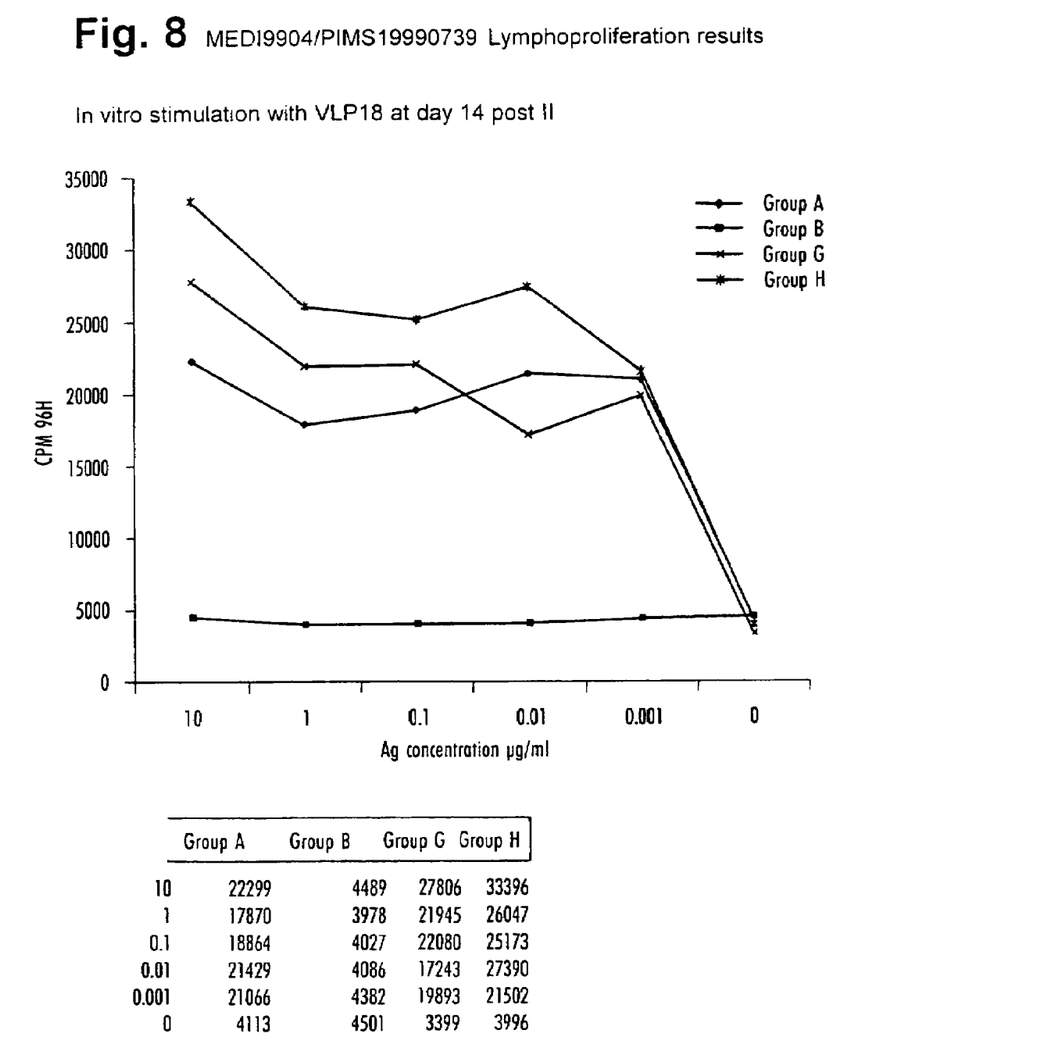

Fig. 8 MEDI9904/PIMS19990739 Lymphoproliferation results

In vitro stimulation with VLP18 at day 14 post II

|   | Group A | Group B | Group G | Group H |
|---|---|---|---|---|
| 10 | 22299 | 4489 | 27806 | 33396 |
| 1 | 17870 | 3978 | 21945 | 26047 |
| 0.1 | 18864 | 4027 | 22080 | 25173 |
| 0.01 | 21429 | 4086 | 17243 | 27390 |
| 0.001 | 21066 | 4382 | 19893 | 21502 |
| 0 | 4113 | 4501 | 3399 | 3996 |

Figure 9:
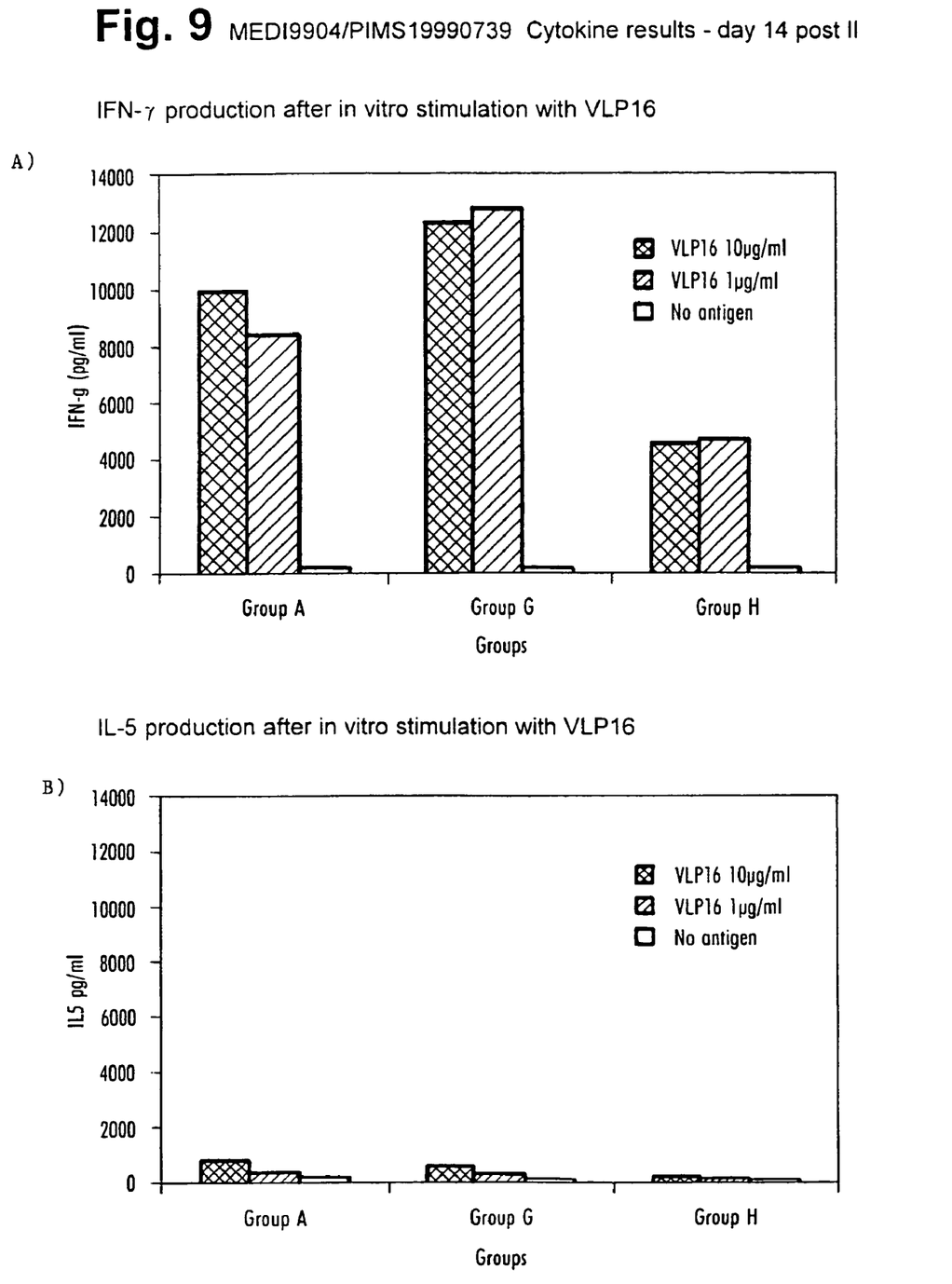

Fig. 9 MEDI9904/PIMS19990739 Cytokine results - day 14 post II

IFN-γ production after in vitro stimulation with VLP16

A)

IL-5 production after in vitro stimulation with VLP16

B)

Fig. 10

VACCINE AGAINST HBV AND HPV

This application is a continuation of application Ser. No. 10/070,468, filed Oct. 1, 2002, now abandoned which is a 371 of International application No. PCT/EP00/08728, filed 06 Sep. 2000.

This invention relates to novel vaccine formulations, methods for preparing them and their use in therapy. In particular the present invention relates to combination vaccines for administration to adolescents.

Papillomavirus are small DNA tumour viruses, which are highly species specific. So far, over 70 individual human papillomavirus (HPV) genotypes have been described. HPVs are generally specific either for skin (e.g. HPV-1 and-2) or mucosal surfaces (e.g. HPV-6 and-11) and usually cause benign tumours (warts) that persist for several months or years. Such benign tumours may be distressing for the individuals concerned but tend not to be life threatening, with a few exceptions.

Some HPVs are also associated with cancers. The strongest positive association between an HPV and human cancer is that which exists between HPV-16 and HPV-18 and cervical carcinoma. Cervical cancer is the most common malignancy in developing countries, with about 500,000 new cases occurring in the world each year. It is now technically feasible to actively combat primary HPV-16 infections, and even established HPV-16-containing cancers, using vaccines. For a review on the prospects for prophylactic and therapeutic vaccination against HPV-16 see Cason J., Clin. Immunother. 1994; 1(4) 293-306 and Hagenesee M. E., Infections in Medicine 1997 14(7) 555-556, 559-564.

Today, the different types of HPVs have been isolated and characterized with the help of cloning systems in bacteria and more recently by PCR amplification. The molecular organisation of the HPV genomes has been defined on a comparative basis with that of the well characterized bovine papillomavirus type 1 (BPV1).

Other HPV serotypes of particular interest are 31, 33 and 45.

Although minor variations do occur, all HPVs genomes described have at least seven early genes, E1 and E7 and two late genes L1 and L2. In addition, an upstream regulatory region harbors the regulatory sequences which appear to control most transcriptional events of the HPV genome.

E1 and E2 genes are involved in viral replication and transcriptional control, respectively and tend to be disrupted by viral integration. E6 and E7, and recent evidence implicate also E5 are involved in viral transformation.

In the HPVs involved in cervical carcinoma such as HPV 16 and 18, the oncogenic process starts after integration of viral DNA. The integration results in the inactivation of genes coding for the capsid proteins L1 and L2 and in installing continuous over expression of the two early proteins E6 and E7 that will lead to gradual loss of the normal cellular differentiation and the development of the carcinoma.

Carcinoma of the cervix is common in women and develops through a pre-cancerous intermediate stage to the invasive carcinoma which frequently leads to death. The intermediate stages of the disease is known as cervical intraepithelial neoplasia and is graded I to III in terms of increasing severity.

Clinically, HPV infection of the female anogenital tract manifests as cervical flat condylomas, the hallmark of which is the koilocytosis affecting predominantly the superficial and intermediate cells of the cervical squamous epithelium. Koilocytes which are the consequence of a cytopathic effect of the virus, appear as multinucleated cells with a perinuclear clear halo. The epithelium is thickened with abnormal keratinisation responsible for the warty appearance of the lesion.

Such flat condylomas when positive for the HPV 16 or 18 serotypes, are high-risk factors for the evolution toward cervical intraepithelial neoplasia (CIN) and carcinoma in situ (CIS) which are themselves regarded as precursor lesions of invasive cervix carcinoma.

WO 96/19496 discloses variants of human papillomavirus E6 and E7 proteins, particularly fusion proteins of E6/E7 with a deletion in both the E6 and E7 proteins. These deletion fusion proteins are said to be immunogenic.

HPV L1 based vaccines are disclosed in WO94/00152, WO94/20137, WO93/02184 and WO94/05792. Such a vaccine can comprise the L1 antigen as a monomer, a capsomer or a virus like particle. Such particles may additionally comprise L2 proteins. L2 based vaccines are described for example in WO93/00436. Other HPV vaccines are based on the Early proteins, such as E7 or fusion proteins such as L2-E7.

Vaccines for the prophylaxis of hepatitis B infections, comprising one or more hepatitis B antigens, are well known. For example the vaccine Engerix-B (Trade Mark) from SmithKline Beecham Biologicals is used to prevent Hepatitis B. This vaccine comprises hepatitis B surface antigen (specifically the 226 amino acid S-antigen described in Harford et. al. in Postgraduate Medical Journal, 1987, 63 (Suppl. 2), p65-70) and is formulated using aluminum hydroxide as adjuvant.

There is a need for effective combination vaccines to prevent diseases to which adolescents are particularly prone.

The present invention provides a vaccine composition comprising:
  (a) a hepatitis B viral (HBV) antigen; and
  (b) a human papillomavirus (HPV) antigen in combination with an adjuvant which is a preferential stimulator of TH1 cell response.

The vaccine composition of the invention is of great benefit for administration to adolescents who may be particularly at risk of HBV, and/or HPV infection.

Optionally the vaccine composition of the invention additionally comprises one or more of a number of other antigens as described below.

It has been found that the vaccine compositions according to the invention surprisingly show no interference, that is to say that the immune response to each antigen in the composition of the invention is essentially the same as that which is obtained by each antigen given individually in conjunction with an adjuvant which is a preferential stimulator of TH1 cell response.

The vaccine Havrix (Trade Mark), also from SmithKline Beecham Biologicals is an example of a vaccine that can be used to prevent hepatitis A infections. It is formulated with aluminium hydroxide as adjuvant. This vaccine comprises an attenuated strain of the HM-175 Hepatitis A virus inactivated with formol (formaldehyde); see Andre et. al. (Prog. med. Virol., vol. 37, p1-24).

As used herein, the term hepatitis A viral (HAV) antigen is used to refer to either a protein derived from hepatitis A virus or an attenuated strain of HAV, optionally inactivated, e.g. with formaldehyde. If the HAV antigen is a protein derived from hepatitis A virus it may optionally be a recombinant protein.

The vaccine Twinrix (Trade Mark) is a combination of a recombinant hepatitis B antigen with the aforementioned inactivated attenuated hepatitis A virus. The vaccine may be used to protect against hepatitis A and hepatitis B simultaneously.

European patent 0 339 667 (Chemo Sero) describes the general concept of combining a hepatitis A antigen and a hepatitis B antigen to make a combination vaccine. In that specification it is stated that the adjuvant which is used is not critical: it must only be capable of enhancing the immune activity to a desired extent and not cause any side-effects. It is stated that aluminium gel may be used, in particular aluminium hydroxide gel and aluminium phosphate gel.

In a further aspect, the invention provides a vaccine composition comprising:

(a) a hepatitis B viral (HBV) antigen;
(b) a human papillomavirus (HPV) antigen; and
(c) a hepatitis A viral (HAV) antigen in combination with an adjuvant which is a preferential stimulator of TH1 cell response.

Such a vaccine is of great benefit for administration to adolescents who may be particularly at risk of HBV, and/or HPV infection, and/or HAV infection.

An immune response may be broadly divided into two extreme categories, being a humoral or cell mediated immune response (traditionally characterized by antibody and cellular effector mechanisms of protection respectively). These categories of response have been termed TH1-type responses (cell-mediated response), and TH2-type immune responses (humoral response).

Extreme TH1-type immune responses may be characterized by the generation of antigen specific, haplotype restricted cytotoxic T lymphocytes, and natural killer cell responses. In mice TH1-type responses are often characterized by the generation of antibodies of the IgG2a subtype, whilst in the human these correspond to IgG1 type antibodies. TH2-type immune responses are characterized by the generation of a range of immunoglobulin isotypes including in mice IgG1.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ve T cell clones by Mosmann and Coffman (Mosmann, T. R. and Coffman, R. L. (1989) *TH1 and TH2 cells: different patterns of lymphokine secretion lead to different functional properties. Annual Review of Immunology*, 7, p145-173). Traditionally, TH1-type responses are associated with the production of the INF-γ cytokines by T-lymphocytes. Other cytokines often directly associated with the induction of TH1-type immune responses are not produced by T-cells, such as IL-12. In contrast, TH2-type responses are associated with the secretion of IL4, IL-5, IL-6, IL-10 and tumour necrosis factor-β (TNF-β).

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement (at least in mice) of the IgG1:IgG2a ratio of antigen specific antibody responses.

Thus, a TH1-type adjuvant is one which stimulates isolated T-cell populations to produce high levels of TH1-type cytokines when re-stimulated with antigen in vitro, and induces antigen specific immunoglobulin responses associated with TH1-type isotype.

Adjuvants which are capable of preferential stimulation of the TH1 cell response are described in International Patent Application No. WO 94/00153 and WO 95/17209. 3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immnunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (as described in European Patent number 0 689 454). 3D-MPL will be present in the range of 10 μg-100 μg preferably 25-50 μg per dose wherein the antigen will typically be present in a range 2-50 μg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with an carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen. Thus vaccine compositions which form part of the present invention may include a combination of QS21 and cholesterol.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. Additionally the oil in water emulsion may contain span 85 and/or lecithin and/or tricaprylin.

In a particularly preferred aspect the antigens in the vaccine composition according to the invention are combined with 3D-MPL and alum.

Typically for human administration QS21 and 3D-MPL will be present in a vaccine in the range of 1 μg-200 μg, such as 10-100 μg, preferably 10 μg-50 μg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The HPV antigen in the composition of the invention is preferably derived from HPV 16 and/or 18, or from HPV 6 and/or 11, or HPV 31, 33 or 45.

In one preferred embodiment the HPV antigen in the vaccine composition according to the invention comprises the major capsid protein L1 of HPV and optionally the L2 protein, particularly from HPV 16 and/or HPV 18. In this embodiment, the preferred form of the L1 protein is a truncated L1 protein. Preferably the L1 is in the form of a virus-like particle (VLP). The L1 protein may be fused to another HPV protein, in particular E7 to form an L1-E7 fusion. Chimeric VLPs comprising L1-E or L1-L2-E are particularly preferred.

In another preferred embodiment, the HPV antigen in the composition of the invention is derived from an E6 or E7 protein, in particular E6 or E7 linked to an immunological fusion partner having T cell epitopes.

In a preferred form of this embodiment of the invention, the immunological fusion partner is derived from protein D of *Heamophilus influenza* B. Preferably the protein D derivative comprises approximately the first 1/3 of the protein, in particular approximately the first N-terminal 100-110 amino acids.

Preferred fusion proteins in this embodiment of the invention comprise Protein D-E6 from HPV 16, Protein D-E7 from HPV 16 Protein D-E7 from HPV 18 and Protein D-E6 from HPV 18. The protein D part preferably comprises the first 1/3 of protein D.

In still another embodiment of the invention, the HPV antigen is in the form of an L2-E7 fusion, particularly from HPV 6 and/or HPV 11.

The proteins of the present invention preferably are expressed in *E. coli*. In a preferred embodiment the proteins are expressed with a Histidine tail comprising between 5 to 9 and preferably six Histidine residues. These are advantageous in aiding purification. The description of the manufacture of such proteins is fully described in co-pending UK patent application number GB 9717953.5.

The HPV antigen in the vaccine composition may be adsorbed onto $Al(OH)_3$. Preferably the L1 VLP is adsorbed onto $Al(OH)_3$.

The hepatitis B viral (HBV) antigen in the composition of the invention is typically hepatitis B surface antigen.

The preparation of Hepatitis B surface antigen (HBsAg) is well documented. See for example, Harford et. al. in Develop. Biol. Standard 54, page 125 (1983), Gregg et. al. in Biotechnology, 5, page 479 (1987), EP-A-0 226 846, EP-A-0 299 108 and references therein.

As used herein the expression 'Hepatitis B surface antigen', abbreviated herein to 'HBsAg' or 'HBS' includes any HBsAg antigen or fragment thereof displaying the antigenicity of HBV surface antigen. It will be understood that in addition to the 226 amino acid sequence of the HBsAg S antigen (see Tiollais et. al. Nature, 317, 489 (1985) and references therein) HBsAg as herein described may, if desired, contain all or part of a pre-S sequence as described in the above references and in EP-A-0 278 940. HBsAg as herein described can also refer to variants, for example the 'escape mutant' described in WO 91/14703. In a further aspect the HBsAg may comprise a protein described as L* in European Patent Application Number 0 414 374, that is to say a protein, the amino acid sequence of which consists of parts of the amino acid sequence of the hepatitis B virus large (L) protein (ad or ay subtype), characterized in that the amino acid sequence of the protein consists of either:
 (a) residues 12-52, followed by residues 133-145, followed by residues 175-400 of the said L protein; or
 (b) residue 12, followed by residues 14-52, followed by residues 133-145, followed by residues 175-400 of the said L protein.

HBsAg may also refer to polypeptides described in EP 0 198 474 or EP 0 304 578.

Normally the HBsAg will be in particle form. It may comprise S protein alone or may be as composite particles, for example (L*,S) wherein L* is as defined above and S denotes the S-protein of hepatitis B surface antigen.

The HBsAg may be adsorbed on aluminium phosphate as described in WO93/24148.

Preferably the hepatitis B (HBV) antigen used in the formulation of the invention is HBsAg S-antigen as used in the commercial product Engerix-B (Trade Mark; SmithKline Beecham Biologicals).

A vaccine comprising hepatitis B surface antigen in conjunction with 3D-MPL was described in European Patent Application 0 633 784.

Examples of antigens from additional pathogens which may be included in the compositions according to the invention are now described.

Epstein Barr Virus (EBV), a member of the herpes virus group, causes infectious mononucleosis as a primary disease in humans. Predominantly it affects children or young adults. More than 90% of the average adult population is infected by EBV that persists for lifetime in peripheral B-lymphocytes. The virus is lifelong produced in the parotid gland and spread primarily by exchange of saliva from individuals who shed the virus. Children infected with EBV are largely asymptomatic or have very mild symptoms, while adolescents and adults who become infected develop typical infectious mononucleosis, characterized by fever, pharyngitis, and adenopathy. People who have been infected maintain anti-EBV antibodies for the remainder of their lives, and are thus immune to further infection.

In addition to its infectious qualities, EBV has been shown to transform lymphocytes into rapidly dividing cells and has therefore been implicated in several different lymphomas, including African Burkitt's lymphoma (BL). EBV may also be involved in causing nasopharyngeal carcinoma (NPC). Worldwide it is estimated that 80,000 cases of nasopharyngeal carcinoma occur and it is more prevalent in ethnic Chinese populations. Infectious mononucleosis is a consequence of primary infection by EBV. It is not a life-threatening disease if additional risk factors are absent.

Four proteins of the EBV viral envelope constituting the so-called membrane antigen complex have been described. They are usually referred to as gp 220/350 or gp 250/350 or simply as gp 250 or 350 (see EP-A-151079). There is convincing evidence that gp 350 and gp 250 induce the production of neutralising antibodies and that antibodies against gp 350 and gp 250 have neutralising capacity. These proteins are thus candidates for a possible EBV vaccine. For further information about the application of gp 250/350 for prophylaxis and treatment of EBV-related diseases see EP 0 173 254.

The major EBV surface glycoprotein gp350/220 infects human target cells through interaction with the cellular membrane protein, CD21. Gp350/220 is the primary target for EBV-neutralising antibodies in humans and some forms of gp350/220 have been shown to protect against EBV-related disease. Preferably a vaccine composition according to the invention comprises gp 350 of EBV although other protective antigens may be used.

HSV-2 is the primary etiological agent of herpes genitalis. HSV-2 and HSV-1 (the causative agent of herpes labialis) are characterized by their ability to induce both acute diseases and to establish a latent infection, primarily in neuronal ganglia cells.

Genital herpes is estimated to occur in about 5 million people in the U.S.A. alone with 500,000 clinical cases recorded every year (primary and recurrent infection). Primary infection typically occurs after puberty and is characterized by the localised appearance of painful skin lesions, which persist for a period of between 2 to 3 weeks. Within the following six months after primary infection 50% of patients will experience a recurrence of the disease. About 25% of patients may experience between 10-15 recurrent episodes of the disease each year. In immunocompromised patients the incidence of high frequency recurrence is statistically higher than in the normal patient population.

Both HSV-1 and HSV-2 virus have a number of glycoprotein components located on the surface of the virus. These are known as gB, gC, gD and gE etc.

When an HSV antigen is included in the composition of the invention this is preferably derived from HSV-2, typically glycoprotein D. Glycoprotein D is located on the viral membrane, and is also found in the cytoplasm of infected cells (Eisenberg R. J. et al; J of Virol 1980, 35, 428-435). It comprises 393 amino acids including a signal peptide and has a molecular weight of approximately 60 kD. Of all the HSV envelope glycoproteins this is probably the best characterized (Cohen et al; J. of Virology, 60, 157-166). In vivo it is known to play a central role in viral attachment to cell membranes. Moreover, glycoprotein D has been shown to be able to elicit neutralising antibodies in vivo (Eing et al J. Med. Virology 127: 59-65). However, latent HSV-2 virus can still be reactivated and induce recurrence of the disease despite the presence of high neutralising antibodies titre in the patients sera.

In one embodiment of the invention there is present a truncated HSV-2 glycoprotein D of 308 amino acids which comprises amino acids 1 through 306 naturally occurring glycoprotein with the addition Asparagine and Glutamine at the C terminal end of the truncated protein devoid of its membrane anchor region. This form of the protein includes the signal peptide which is cleaved to yield a mature 283 amino acid protein. The production of such a protein in Chinese Hamster ovary cells has been described in Genentech's European patent EP-B-139 417.

The recombinant mature HSV-2 glycoprotein D truncate is preferably used in the vaccine formulations of the present invention and is designated rgD2t.

A combination of this HSV-2 antigen in combination with the adjuvant 3D-MPL has been described in WO 92/16231.

In a preferred aspect the vaccine composition of the invention additionally comprises a Varicella Zoster viral antigen (VZV antigen). Suitable antigens of VZV for inclusion in the vaccine formulation include gpI-V described by Longnecker et al., Proc Natl Acad Sci USA 84, 4303-4307 (1987).

In a preferred embodiment gpI (see Ellis et al., U.S. Pat. No. 4,769,239) is used. See also European Patent No. 0 405 867 B1.

In another preferred aspect the vaccine composition of the invention additionally comprises a human cytomegalovirus (HCMV) antigen. HCMV is a human DNA virus belonging to the family of herpes viruses. HCMV is endemic in most parts of the world. Among two populations, HCMV is responsible for serious medical conditions. HCMV is a major cause of congenital defects in new borns. The second population at risk are immunocompromised patients such as those suffering from HIV infection and those patients undergoing transplantations. The clinical disease causes a variety of symptoms including fever, hepatitis, pneumonitis and infectious mononucleosis. A preferred antigen for use in a vaccine against HCMV is gB685** as described in WO 95/31555. Immunogens for use in HCMV vaccines are also provided by pp65, an HCMV Matrix Protein as described in WO 94/00150 (City of Hope).

In one preferred aspect the vaccine composition of the invention additionally comprises both a VZV and an HCMV antigen, in particular those antigens described above.

In another preferred aspect the vaccine composition of the invention additionally comprises a *Toxoplasma gondii* antigen. *Toxoplasma gondii* is an obligate intracellular protozoan parasite responsible for toxoplasmosis in warm-blooded animals, including man. Although it is generally clinically asymptomatic in healthy individuals, toxoplasmosis may cause severe complications in pregnant women and immunocompromised patients. A preferred antigen for use in a vaccine against *Toxoplasma gondii* is SAG1 (also known as P30) as described in WO96/02654 or Tg34 as described in WO92/11366.

In one preferred aspect the vaccine composition of the invention additionally comprises either a VZV antigen or an HCMV antigen combined with a *Toxoplasma gondii* antigen, in particular those antigens described above.

In a preferred aspect the vaccine composition of the invention is a multivalent vaccine, for example a tetra-or pentavalent vaccine.

The formulations of the present invention are very effective in inducing protective immunity, even with very low doses of antigen (e.g. as low as 5 μg rgD2t).

They provide excellent protection against primary infection and stimulate, advantageously both specific humoral (neutralising antibodies) and also effector cell mediated (DTH) immune responses.

The present invention in a further aspect provides a vaccine formulation as herein described for use in medical therapy, particularly for use in the treatment or prophylaxis of human papillomavirus infections and hepatitis B virus infections.

The vaccine of the present invention will contain an immunoprotective quantity of the antigens and may be prepared by conventional techniques.

Vaccine preparation is generally described in Pharmaceutical Biotechnology, Vol.61 Vaccine Design—the subunit and adjuvant approach, edited by Powell and Newman, Plenurn Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed. Generally, it is expected that each dose will comprise 1-1000 µg of protein, preferably 2-100 µg, most preferably 4-40 µg. An optimal amount for a particular vaccine can be ascertained by standard studies involving observation of antibody titres and other responses in subjects. Following an initial vaccination, subjects may receive a boost in about 4 weeks.

In addition to vaccination of persons susceptible to HPV or HBV infections, the pharmaceutical compositions of the present invention may be used to treat, immunotherapeutically, patients suffering from the said viral infections.

In a further aspect of the present invention there is provided a method of manufacture as herein described, wherein the method comprises mixing a human papilloma virus antigen and a hepatitis B virus antigen with a TH-1 inducing adjuvant, for example 3D-MPL and, preferably, a carrier, for example alum.

If desired, other antigens may be added, in any convenient order, to provide multivalent vaccine compositions as described herein.

The following example illustrates but does not limit the invention.

EXAMPLE 1

Comparative Immunogenicity of HPV Ags/HBs Combos Fomulated with Alum/3D-MPL

Introduction

An immunogenicity study was performed in Balb/C mice using four different antigens:
1. HPV16 L1 Virus Like Particule (VLP-16)
2. HPV18 L1 Virus Like Particule (VLP18)
3. PD 1/3 16E7 2M from HPV-16 (E7)
4. HBsAg formulated with Alum/3D-MPL (AS04) using pre adsorbed monobulks of antigen or 3D-MPL on $Al(OH)_3$ or $AlPO_4$.

3D-MPL/$Al(OH)_3$ formulations are referred to as AS04D whereas 3D-MPL/$AlPO_4$ based formulations are referred to as AS04C.

The following vaccines were assessed:
1. VLP16+VLP18 AS04D;
2. E7 based formulations,
3. HBs AS04C and the potential to combine these vaccines was evaluated.

The aims of this experiment were as follows:
1) To compare the immunogenicity of different AS04 combinations of either VLP16+VLP18 or E7 and HBs Ag.
2) As the monovalent vaccines are either formulated in AS04C or AS04D:
    to compare the immunogenicity of different HBs AS04 formulations made of $AlPO_4$ or a mix of $AlPO_4$/$Al(OH)_3$ with different ratios of Alum forms; and
    to evaluate the effect of the adsorption of 3D-MPL on a fraction of $Al(OH)_3$ and $AlPO_4$ versus 3D-MPL/$Al(OH)_3$ in combination containing VLPs or E7 antigens.

The experimental protocol is fully described in the Material and Methods section.

In summary, groups of 10 mice were immunised intramuscularly twice a week at 3 week intervals with various Ag based formulations (1/10HD). Antibody response to HBs, E7 and VLPs Ag and the isotypic profile induced by vaccination were monitored by ELISA at day 14 post II. At the same timepoint, the CMI (lymphoproliferative response or the cytokine production (IFNγ/IL5)) was analysed after in vitro restimulation of splenic cells with either HBs, VLPs or E7 antigen.

Materials and Methods

Formulation

Formulation Compositions

VLP16, VLP18, PD1/3-HPV16E7-His, and HBs on AS04C or AS04D.

| | Components used | |
|---|---|---|
| Component | Concentration | Buffer |
| HPV 16 VLP | 560 µg/ml | Tris 20 mM/NaCl 500 mM |
| HPV 18 VLP | 550 µg/ml | NaCl 500 mM/NaPO$_4$ 20 mM |
| AL(OH)$_3$ | 10380 µg/ml | H$_2$O |
| PD1/3-HPV 16 E7-His | 1170 µg/ml | PO$_4$ 20 mM |
| HBs | 1219 µg/ml | PO$_4$ 10 mM/NaCl 150 mM |
| 3D-MPL | 1170 µg/ml | Water For Injection |
| AlPO$_4$ | 5 mg/ml | NaCl 150 mM |

Adsorption a) VLP Adsorption.

VLP 16 and VLP 18 purified bulk is added to $Al(OH)_3$ at 2 µg VLP/10 µg $Al(OH)_3$. The mixture is stored between 2-8° C. until final formulation.

b) HBs Adsorption.

2 µg Hbs are mixed with 40 µg $AlPO_4$. The mixture is stored between 2-8° C. until final formulation.

2 µg Hbs are mixed with 10 µg $AlPO_4$. The mixture is stored between 2-8° C. until final formulation.

c) PD1/3-HPV16E7-His Adsorption.

2 µg E7 are mixed with 10 µg $Al(OH)_3$. The mixture is stored between 2-8° C. until final formulation.

d) 3D-MPL Adsorption.

5 µg 3D-MPL are mixed with 10 µg $Al(OH)_3$. The mixture is stored between 2-8° C. until final formulation.

5 µg 3D-MPL are mixed with 10 µg $AlPO_4$. The mixture is stored between 2-8° C. until final formulation.

2.5 µg 3D-MPL are mixed with 5 µg $Al(OH)_3$. The mixture is stored between 2-8° C. until final formulation.

2.5 µg 3D-MPL are mixed with 5 µg $AlPO_4$. The mixture is stored between 2-8° C. until final formulation.

Formulation

H$_2$O and NaCl are mixed (10× concentrated) and after 10 minutes of agitation at room temperature, the different components are added: adsorbed antigen, adsorbed 3D-MPL and $Al(OH)_3$ (See table below). They are shaken at room temperature for 10 minutes and stored at 4° C. until injection. The in vitro characterization of the formulation can then be performed.

Table of groups and details of formulations

| Group | Antigen(s) Type | µg | Immunostimulants Type | µg | Vehicle Type | µg |
|---|---|---|---|---|---|---|
| A | VLP16 | 2 | | | Al(OH)$_3$ | 10 |
| | VLP18 | 2 | | | Al(OH)$_3$ | 10 |
| | | | 3D-MPL | 5 | Al(OH)$_3$ | 10 |
| | | | | | | 20 |
| B | HPV16E7 | 2 | | | Al(OH)$_3$ | 10 |
| | | | 3D-MPL | 5 | Al(OH)$_3$ | 10 |
| | | | | | | 30 |
| C | HBs | 2 | | | AlPO$_4$ | 40 |
| | | | 3D-MPL | 5 | AlPO$_4$ | 10 |
| D | HBs | 2 | | | AlPO$_4$ | 10 |
| | | | 3D-MPL | 5 | AlPO$_4$ | 10 |
| | | | | | Al(OH)$_3$ | 30 |
| E | HBs | 2 | | | AlPO$_4$ | 10 |
| | | | 3D-MPL | 5 | Al(OH)$_3$ | 10 |
| | | | | | Al(OH)$_3$ | 30 |
| F | E7 | 2 | | | Al(OH)$_3$ | 10 |
| | HBs | 2 | | | AlPO$_4$ | 10 |
| | | | 3D-MPL | 5 | Al(OH)$_3$ | 10 |
| | | | | | Al(OH)$_3$ | 20 |
| G | VLP16 | 2 | | | Al(OH)$_3$ | 10 |
| | VLP18 | 2 | | | Al(OH)$_3$ | 10 |
| | HBs | 2 | | | AlPO$_4$ | 10 |
| | | | 3D-MPL | 5 | Al(OH)$_3$ | 10 |
| | | | | | Al(OH)$_3$ | 10 |
| H | VLP16 | 2 | | | Al(OH)$_3$ | 10 |
| | VLP18 | 2 | | | Al(OH)$_3$ | 10 |
| | HBs | 2 | | | AlPO$_4$ | 10 |
| | | | 3D-MPL | 2.5 | Al(OH)$_3$ | 5 |
| | | | 3D-MPL | 2.5 | AlPO$_4$ | 5 |
| | | | | | Al(OH)$_3$ | 10 |

Mice Serology

Anti-HBs Serology

The quantitation of anti-HBs antibodies was performed by ELISA using HBs (Hep 286) as the coating antigen. Antigen and antibody solutions were used at 50 µl per well. The antigen was diluted at a final concentration of 1 µg/ml in PBS and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin and 0.1% Tween 20 (saturation buffer). Two-fold dilutions of sera (starting at 1/100 dilution) in the saturation buffer were added to the HBs-coated plates and incubated for 1 hr 30 min at 37° C. The plates were washed four times with PBS 0.1% Tween 20 and biotin-conjugated anti-mouse Ig (Amersham, UK) diluted 1/1500 or IgG1, IgG2a, IgG2b (IM-TECH, USA) diluted respectively at 1/4000, 1/8000, 1/4000 in saturation buffer were added to each well and incubated for 1 hr 30 min at 37° C. After a washing step, streptavidin-biotinylated peroxydase complex (Amersham, UK) diluted 1/1000 in saturation buffer was added for an additional 30 min at 37° C. Plates were washed as above and incubated for 20 min with a solution of o-phenylenediarnine (Sigma) 0.04% H$_2$O$_2$ 0.03% in 0.1% tween 20 0.05M citrate buffer pH4.5. The reaction was stopped with H$_2$SO$_4$ 2N and read at 490/630 nm. ELISA titers were calculated from a reference by SoftmaxPro (using a four parameters equation) and expressed in EU/ml.

Anti-E7 Serology

Quantitation of anti-E7 antibody was performed by ELISA using PD1/3 16E7 2M as coating antigen. Antigen and antibody solutions were used at 100 µl per well. The antigen was diluted at a final concentration of 0.5 µg/ml in PBS and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin and 0.1% Tween 20 (saturation buffer). Two-fold dilutions of sera (starting at 1/100 or 1/400 dilution) in the saturation buffer were added to the E7-coated plates and incubated for 1 hr 30 min at 37° C. The plates were washed four times with PBS 0.1% Tween 20 and biotin-conjugated anti-mouse Ig, IgG1, IgG2a, IgG2b (Amersham, UK) diluted 1/1500 in saturation buffer were added to each well and incubated for 1 hr 30 min at 37° C. After washing step, streptavidin-biotinylated peroxydase complex (Amersham, UK) diluted 1/5000 in saturation buffer was added for an additional 30 min at 37° C. Plates were washed as above and incubated for 20 min with a solution of Tetramethyl benzidine (TMB) (Biorad, USA) 2-fold diluted in Citrate buffer (0.1M pH=5.8). The reaction was stopped with H$_2$SO$_4$ 0.5 N and read at 450/630 nm. ELISA titers were calculated from a reference by SoftmaxPro (using a four parameters equation) and expressed in EU/ml.

Anti-VLP16 and Anti-VLP18 Serology

The quantitation of anti-VLP16 and anti-VLP18 antibodies was performed by ELISA using VLP16 503/1 (20/12/99) ands VLP18 504/2 (25/10/99F) as coating antigens. The antigen and antibody solutions were used at 50 µl per well. The antigen was diluted at a final concentration of 0.5 µg/ml in PBS and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin. Two-fold dilutions of sera (starting at 1/400 dilution) in the saturation buffer were added to the VLPs-coated plates and incubated for 1 hr 30 min at 37° C. The plates were washed four times with PBS 0.1% Tween 20 and biotin-conjugated anti-mouse Ig (Amersham, UK) diluted 1/1500 in saturation buffer were added to each well and incubated for 1 hr 30 min at 37° C. After a washing step, streptavidin-biotinylated peroxydase complex (Amersham, UK) diluted 1/1000 in saturation buffer was added for an additional 30 min at 37° C. Plates were washed as above and incubated for 20 min with a solution of o-phenylenediamine (Sigma) 0.04% H$_2$O$_2$ 0.03% in 0.1% tween 20 0.05M citrate buffer pH4.5. The reaction was stopped with H$_2$SO$_4$ 2N and read at 490/630 nm. ELISA titers were calculated from a reference by SoftmaxPro (using a four parameters equation) and expressed in EU/ml.

T Cell Proliferation

Two weeks after the second immunisation, mice were killed, spleens were removed aseptically and pooled (1 pool of 5 organs per group). Cell suspensions were prepared in RPMI 1640 medium (GIBCO) containing 2 mM L-glutamine, antibiotics, $5 \times 10^{-5}$M 2-mercaptoethanol, and 1% syngeneic normal mouse serum. Splenic cells were cultured at a final concentration of $2 \times 10^6$ cells/ml in 200 µl in round-bottomed 96 wells-plates with different concentrations (10-0.03 µg/ml) of each of the Ag (VLPs, E7 or HBs antigen). Each test was carried out in quadriplicate. After 96 hr of culture at 37° C. under 5% CO$_2$, the cells were pulsed for 18 hr with $^3$H-Thymidine (Amersham, UK, 5 Ci/mmol) at 0.5 µCi/well and then harvested on Unifilter plates (Packard) with a cell harvester. Incorporated radioactivity was measured in a scintillation counter (Topcount, Packard). Results are expressed in cpm (mean cpm in quadriplicate wells) or as stimulation indices (mean cpm in cultures of cells with antigen/mean cpm in cultures of cells without antigen).

Cytokine Production

Two weeks after the second immunisation, mice were killed, spleens were removed aseptically and pooled. Cell suspensions were prepared in RPMI 1640 medium (GIBCO) containing 2 mM L-glutamine, antibiotics, $5 \times 10^{-5}$M 2-mercaptoethanol, and 5% foetal calf serum. Cells were cultured at a final concentration of $5 \times 10^6$ cells/ml, in 1 ml per flat-bottomed 24 wells-plates with different concentrations (10-1 µg/ml) of each of the Ag (VLPs, E7 or HBs antigen). Supernatants were harvested 96 hrs later and frozen until tested for the presence of IFNγ and IL5 by Elisa.

IFNγ (Genzyme)

Quantitation of IFNγ was performed by Elisa using reagents from Genzyme. Samples and antibody solutions were used at 50 µl per well. 96-wells microtiter plates (Maxisorb Immuno-plate, Nunc, Denmark) were coated overnight at 4° C. with 50 µl of hamster anti-mouse IFNγ diluted at 1.5 µg/ml in carbonate buffer pH 9.5. Plates were then incubated for 1 hr at 37° C. with 100 µl of PBS containing 1% bovine serum albumin and 0.1% Tween 20 (saturation buffer). Two-fold dilutions of supernatant from in vitro stimulation (starting at 1/2) in saturation buffer were added to the anti-IFNγ-coated plates and incubated for 1 hr 30 min at 37° C. The plates were washed 4 times with PBS Tween 0.1% (wash buffer) and biotin-conjugated goat anti-mouse IFNγ diluted in saturation buffer at a final concentration of 0.5 µg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 µl of TMB (Biorad) for 10 min. The reaction was stopped with $H_2SO_4$ 0.4N and read at 450/630 nm. Concentrations were calculated using a standard curve (mouse IFNγ standard) by SoftmaxPro (four parameters equation) and expressed in pg/ml.

IL5 (Pharmingen)

Quantitation of IL5 was performed by Elisa using reagents from Pharmingen. Samples and antibody solutions were used at 50 µl per well. 96-wells microtiter plates (Maxisorb Immuno-plate, Nunc, Denmark) were coated overnight at 4° C. with 50 µl of rat anti-mouse IL5 diluted at 1 µg/ml in carbonate buffer pH 9.5. Plates were then incubated for 1 hr at 37° C. with 100 µl PBS containing 1% bovine serum albumin and 0.1% tween 20 (saturation buffer). Two-fold dilutions of supernatant from in vitro stimulation (starting at 1/2) in saturation buffer were added to the anti-IL-5-coated plates and incubated for 1 hr 30 min at 37° C. The plates were washed 4 times with PBS Tween 0.1% (wash buffer) and biotin-conjugated rat anti-mouse IL5 diluted in saturation buffer at a final concentration of 1 µg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 µl of TMB (Biorad) for 15 min. The reaction was stopped with $H_2SO_4$ 0.4N and read at 450/630 nm. Concentrations were calculated using a standard curve (recombinant mouse IL-5) by SoftmaxPro (four parameters equation) and expressed in pg/ml.

Groups

Groups of 10 Balb/C mice were immunised intramuscularly with the following formulations:

TABLE 1

Groups and formulations

| GROUP | FORMULATION |
|---|---|
| A | VLP16 2 µg/VLP18 2 µg/3D-MPL 5 µg/Al(OH)3 50 µg |
| B | 16E7 2 µg/3D-MPL 5 µg/Al(OH)3 50 µg |
| C | HBs 2 µg/3D-MPL 5 µg/AlPO4 50 µg |
| D | HBs 2 µg/3D-MPL 5 µg/AlPO4 20 µg/Al(OH)3 30 µg |
| E | HBs 2 µg/3D-MPL 5 µg/AlPO4 10 µg/Al(OH)3 40 µg |
| F | 16E7 2 µg/HBS 2 µg/3D-MPL 5 µg/Al(OH) 40 µg/AlPO4 10 µg |
| G | VLP16 2 µg/VLP 18 2 µg/HBs 2 µg/3D-MPL 5 µg/Al(OH)3 40 µg/AlPO4 10 µg |
| H | VLP16 2 µg/VLP 18 2 µg/HBs 2 µg/3D-MPL 5 µg/Al(OH)3 35 µg/AlPO4 15 µg |

Details of formulation are described above in the table in Materials and Methods.

Results

1. Serology a) Anti-HBs Response:

Humoral responses (Ig and isotypes) were measured by Elisa using HBsAg (Hep286) as coating antigen. Day 14 post II sera were analysed.

FIG. 1 shows the anti-HBs antibody responses measured on individual sera on day 14 post II.

No difference was observed in the anti-HBs antibody response between the protocols applied to adsorb the 3D-MPL: on $Al(OH)_3$ alone or $AlPO_4$ alone (groups C, D, E) with different ratios of $Al(OH)_3$ and $AlPO_4$ in the vaccine (GMT of 27905 EU/ml versus 30832 or 26670 EU/ml).

A slightly lower anti-HBs antibody response is observed in the combination groups G and H containing the VLPs and the HBs antigen compared to HBs alone (group C) (GMT respectively of 10635 or 15589 EU/ml versus 27905 EU/ml). Anti-HBs GMT obtained in the E7/HBs combination reached 19235 EU/ml.

Before statistical analysis, a T-Grubbs test was applied on each population for data exclusion. One mouse in group C was eliminated for analysis.

A one-way-analysis of variance was performed on anti-HBs titers after log transformation of post II data. Significant differences were observed between formulations (p-value=0.0108) and the Student Newman Keuls test was then applied for multiple comparisons. No statistically significant difference was observed between the group H (VLP/HBs) or group F (HBs/E7) combination versus the group C (HBs AS04C). A statistically significant difference was shown between the group G (VLP/HBs) and the group C (HBs AS04C) (p value=0.0291) however the 95% confidence intervals of the 2 groups overlap and the difference which reaches a 2.5 ratio might not be biologically relevant.

The isotypic repartition analysed on pooled sera was as follows and showed no major differences between the 6 groups.

| | Isotypic repartition (%) | | |
|---|---|---|---|
| | IgG1 | IgG2a | IgG2b |
| Group C | 59 | 31 | 10 |
| Group D | 69 | 19 | 12 |
| Group E | 66 | 19 | 15 |
| Group F | 61 | 22 | 17 |

-continued

| | Isotypic repartition (%) | | |
|---|---|---|---|
| | IgG1 | IgG2a | IgG2b |
| Group G | 61 | 30 | 9 |
| Group H | 46 | 29 | 25 | b) Anti-E7 Response:

Humoral responses (Ig and isotypes) were measured by Elisa using PD1/3 16E7 2M as the coating antigen. Day 14 post II sera of group B and F were analysed.

FIG. 2 shows the anti-E7 antibody responses measured on individual sera at day 14 post II:

A slight decrease was observed in the anti-E7 response with a two fold decrease in GMT for HBs/E7 combinations compared to E7 alone (9626 versus 22447 EU/ml). This was established as statistically insignificant using the Student Newman Keuls test.

No difference was observed in the isotypic profile induced by the two formulations: mainly IgG1 response (97-98% of IgG1) as reported in the table below.

The isotypic repartition analysed on pooled sera was as follows:

| | Isotypic repartition (%) | | |
|---|---|---|---|
| | IgG1 | IgG2a | IgG2b |
| Group B | 98 | 0 | 1 |
| Group F | 97 | 1 | 2 | c) Anti-VLP16 Response:

Humoral responses (Ig) were measured by Elisa using VLP16 503-1 (20/12/99) as the coating antigen. Day 14 post II sera were analysed.

FIG. 3 shows anti-VLP16 Ig antibody responses measured on individual sera on day 14 post II.

Similar anti-VLP16 titers were obtained after immunisation with the combination of HBs and VLPs (group G and H) as with the monovalent VLPs formulation (group A) (GMT of 19570 or 23448 EU/ml versus 30311 EU/ml)

Equivalent titers were observed between the two combinations prepared using either ways to adsorb the 3D-MPL: Al(OH)$_3$ alone (group G) compared to mixed adsorption on Al(OH)$_3$ and AlPO$_4$ (group H) (GMT of 19570 EU/ml versus 23448 EU/ml).

These differences were shown as statistically not significant using one-way analysis of variance test.

d) Anti-VLP18 Response:

Humoral responses (Ig) were measured by Elisa using VLP18 504-2 (25/10/99) as the coating antigen. Day 14 post II sera were analysed.

FIG. 4 shows the anti-VLP18 Ig antibody response measured on individual sera on day 14 post II Similar anti-VLP18 titers were obtained after immunisation with the combination of HBs and VLPs (group G and H) or with the monovalent VLPs formulations (group A) (GMT of 37285 or 51202 EU/ml versus 56504 EU/ml) Equivalent titers (group G and H) were observed between the combination prepared using either ways to adsorb the 3D-MPL: Al(OH)$_3$ alone (group G) compared to mixed adsorption on Al(OH)$_3$ and AlPO$_4$ (group H).

These differences were shown as statistically not significant using one-way analysis of variance test.

2. Cell Mediated Immune Response

Cell-mediated immune responses (lymphoproliferation, IFN$\gamma$/IL5 production) were evaluated at day 14 post II after in vitro restimulation of splenic cells with either HBs, E7 or VLPs antigens. For each group of mice, pools of 5 organs were constituted.

The experimental procedure is fully described above in Material and Methods.

3. Cytokine Production a) In vitro Restimulation with HBs

FIG. 5 shows the cytokine production monitored in splenic cells after 96 h in vitro restimulation with HBs.

Low IFN-$\gamma$ and IL5 production was observed for all groups but as shown in Table 2 higher production of IFN-$\gamma$ are observed compared to IL-5 production with IFN-$\gamma$/IL-5 ratio indicating that a comparable TH1 response is induced with the monovalent and combined vaccines. The group C results should not be taken into account as data below the threshold may indicate absence of antigen for restimulation.

TABLE 2

| | IFN-$\gamma$/IL-5 ratio after in vitro restimulation with HBs. | | | | | |
|---|---|---|---|---|---|---|
| Ratio IFN-$\gamma$/IL-5 | Group C | Group D | Group E | Group F | Group G | Group H |
| HBs 10 µg/ml | 0.3 | 4.0 | 9.4 | 7.9 | 7.9 | 6.6 |
| HBs 1 µg/ml | 0.4 | 3.7 | 1.5 | 4.0 | 4.0 | 5.0 | b) In vitro Restimulation with E7

FIG. 6 shows the cytokine production monitored in splenic cells after 96 h in vitro restimulation with E7 antigen.

A dose range effect was observed when comparing the 10 µg and 1 µg Ag dose for restimulation.

A non-specific response was observed for HPV16/18 L1 VLPs immunised groups using 10 µg of Ag for restimulation.

The IFN-$\gamma$ is produced in a much higher concentration compared to IL-5 (Table 3) indicating a clear TH-1 profile of the immune response in all groups evaluated (monovalent versus combination).

TABLE 3

IFN-γ/IL-5 ratio after in vitro restimulation with E7.

| Ratio IFN/IL-5 | Group B | Group F |
| --- | --- | --- |
| E7 10 μg/ml | 17.7 | 12.9 |
| E7 1 μg/ml | 8.9 | 1.2 | c) In vitro Restimulation with VLP16 and 18

FIGS. 7 and 8 show the lymphoproliferation after in vitro restimulation with VLP16 or VLP18 on day 14 post II.

Comparable profiles were observed for all the formulations containing VLPs (Integrated Stimulated Indexes between 12-29) with cpm around 30000 for 10 μg Ag restimulation dose, indicating the absence of interference between the different formulations on this read-out.

FIG. 9 shows the cytokine production monitored in splenic cells after 96 h in vitro restimulation with VLP16.

Figure 10:
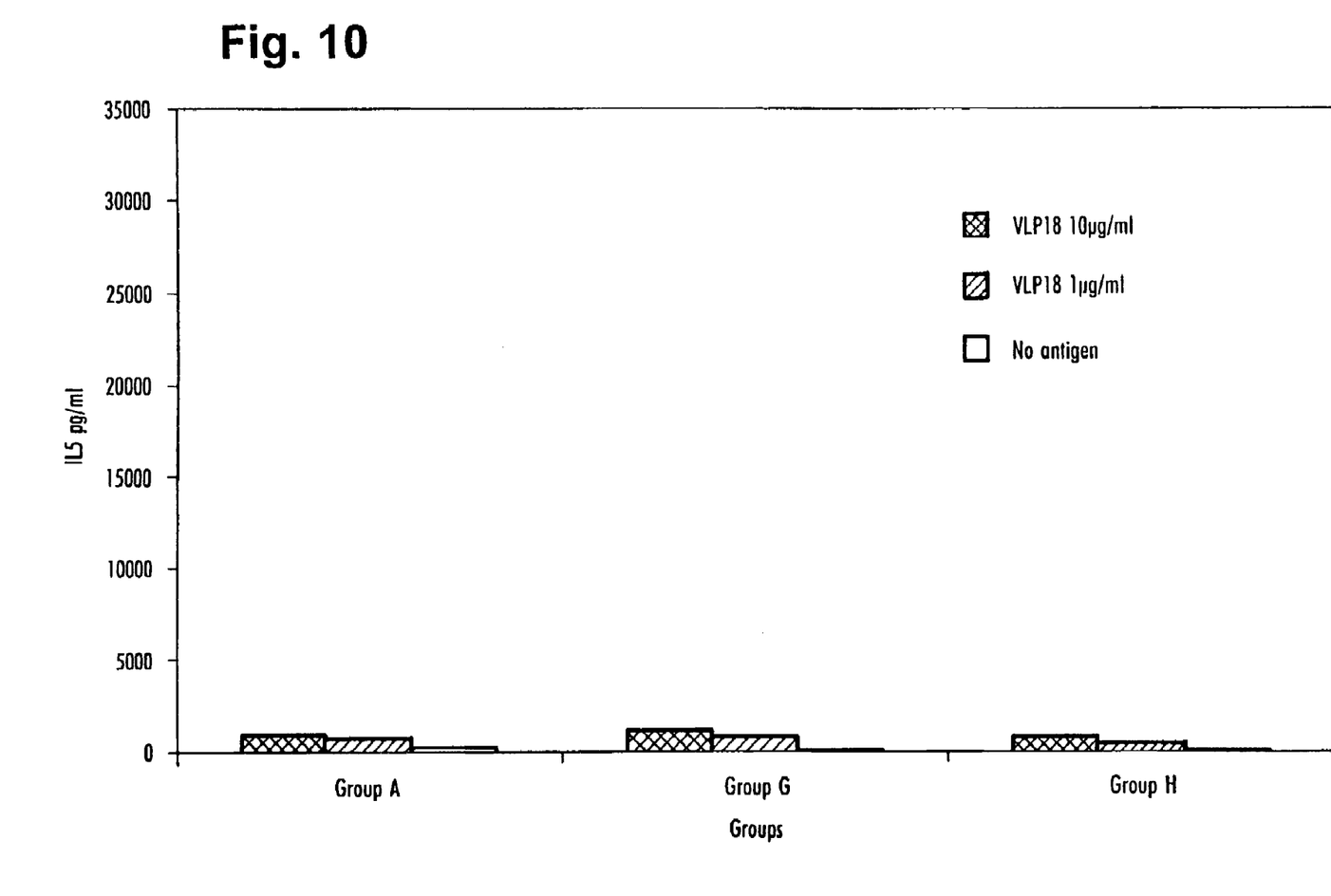

FIG. 10 shows the cytokine production monitored in splenic cells after 96 h in vitro restimulation with VLP18.

No dose range effect has been observed using 10 μg and 1 μg Ag dose for restimulation with either VLP antigens on both cytokine production.

A clear TH1 profile was observed with all formulations.

TABLE 5

IFN-γ/IL-5 ratio after in vitro restimulation with VLP16 and VLP18.

| Ratio IFN/IL-5 | Group A | Group G | Group H |
| --- | --- | --- | --- |
| VLP16 10 μg/ml | 12.0 | 19.9 | 16.5 |
| VLP16 1 μg/ml | 22.1 | 37.9 | 23.2 |
| VLP18 10 μg/ml | 20.5 | 17.9 | 13.4 |
| VLP18 1 μg/ml | 21.8 | 23.7 | 21.0 |

CONCLUSIONS

The effect of the combination of VLPs/HBs or E7/HBs Ag formulated in AS04 on the immunogenicity was evaluated in Balb/C mice:

Regarding the serological analysis, no interference of the Ag combination was observed on anti-HBs, anti-E7 and anti-VLPs serology.

The combination of VLPs and HBs or E7 and HBs antigens did not interfere with the isotypic profile of the antibody response displayed by the monovalent vaccine.

The method of adsorption of 3D-MPL (Al(OH)$_3$, AlPO$_4$, or mixtures of Al(OH)$_3$ and AlPO$_4$) did not interfere with the serological results.

In the lymphoproliferation assays, results were available after restimulation with the VLPs. In these groups, no negative effect of the combination of Ag was observed on the proliferative response.

For the cytokines evaluation, low cytokine production (IL-5 and IFN-γ) was obtained after restimulation with HBs Ag but responses were comparable in the monovalent and combined vaccines. After restimulation with E7 or with VLPs, comparable cytokine levels were produced respectively in the E7/HBs or in the VLP/HBs combination as compared to monovalent groups. The TH-1 profile observed with each monovalent vaccine was conserved in the combination vaccine groups.

The invention claimed is:

1. A vaccine composition comprising:
   (a) a hepatitis B viral antigen;
   (b) an HPV-16 L1 antigen or HPV-16 VLP comprising an HPV-16 L1 antigen; and
   (c) an HPV-18 L1 antigen or HPV-18 VLP comprising an HPV-18 L1 antigen;
   in conjunction with an adjuvant which is a preferential stimulator of TH1 cell response wherein the vaccine composition stimulates a TH1-type immune response.

2. A vaccine composition according to claim 1 which additionally comprises a carrier.

3. A vaccine composition according to claim 1 in which the preferential stimulator of TH1-cell response is selected from the group of adjuvants comprising: 3D-MPL, 3D-MPL wherein the size of the particles of 3D-MPL is preferably about or less than 100 nm, QS21, a mixture of QS21 and cholesterol, and a CpG oligonucleotide.

4. A vaccine composition according to claim 3 in which the preferential stimulator of TH1-cell response is 3D-MPL.

5. A vaccine composition according to claim 1 in which the Hepatitis B antigen is hepatitis B surface antigen.

6. A vaccine composition consisting essentially of:
   (a) a hepatitis B viral antigen;
   (b) an HPV-16 L1 antigen or HPV-16 VLP comprising an HPV-16 L1 antigen; and
   (c) an HPV-18 L1 antigen or HPV-18 VLP comprising an HPV-18 L1 antigen;
   in conjunction with an adjuvant which is a preferential stimulator of TH1 cell response wherein the vaccine composition stimulates a TH1-type immune response.

7. A vaccine composition consisting of:
   (a) a hepatitis B viral antigen;
   (b) an HPV-16 L1 antigen or HPV-16 VLP comprising an HPV-16 L1 antigen;
   (c) an HPV-18 L1 antigen or HPV-18 VLP comprising an HPV-18 L1 antigen; and
   (d) an aqueous carrier in conjunction with an adjuvant which is a preferential stimulator of TH1 cell response wherein the vaccine composition stimulates a TH1-type immune response.

* * * * *